United States Patent
Chernov et al.

(10) Patent No.: US 10,117,705 B2
(45) Date of Patent: Nov. 6, 2018

(54) OPTICAL RECOGNITION OF TISSUE AND VESSELS

(75) Inventors: Boris Chernov, Saint-Petesburg (RU); Nataliya Chernova, legal representative, Saint-Petersburg (RU); Igoris Misuchenko, Saint-Petersburg (RU); Georgy Martsinovskiy, Saint-Petersburg (RU); Mikhail Verbitsky, Stoughton, MA (US)

(73) Assignee: COVIDIEN LP, Mansfield, MA (US)

( * ) Notice: Subject to any disclaimer, the term of this patent is extended or adjusted under 35 U.S.C. 154(b) by 342 days.

(21) Appl. No.: 13/108,196

(22) Filed: May 16, 2011

(65) Prior Publication Data
US 2012/0296205 A1 Nov. 22, 2012

(51) Int. Cl.
*A61B 6/00* (2006.01)
*A61B 18/14* (2006.01)
(Continued)

(52) U.S. Cl.
CPC .......... *A61B 18/1445* (2013.01); *A61B 90/30* (2016.02); *A61B 1/00137* (2013.01);
(Continued)

(58) Field of Classification Search
CPC ................ A61B 18/1445; A61B 90/30; A61B 2090/3941; A61B 2018/00982;
(Continued)

(56) References Cited

U.S. PATENT DOCUMENTS

D249,549 S    9/1978  Pike
4,126,136 A   11/1978 Auth et al.
(Continued)

FOREIGN PATENT DOCUMENTS

CN    201299462    9/2009
DE      2415263   10/1975
(Continued)

OTHER PUBLICATIONS

PCT Search Report for International Application PCT/US2012/038104 dated Jul. 10, 2012.
(Continued)

*Primary Examiner* — Amanda Lauritzen Moher
*Assistant Examiner* — Lisa Kinnard

(57) ABSTRACT

Methods and apparatus for optically recognizing tissue parameters during an energy-based tissue-sealing procedure involve grasping tissue with a tissue-sealing instrument, illuminating the grasped tissue or tissue adjacent to the grasped tissue with light, analyzing the light that is transmitted, scattered, or reflected by the tissue, and recognizing the tissue based on the result of analyzing the light. The wavelength of the light may be selected so that a vessel is sufficiently recognizable in tissue containing the vessel. A marker may also be introduced into fluid flowing in the vessel to increase the contrast between the vessel and tissue containing the vessel. Analyzing the light includes analyzing the spatial and spectral distribution of light. Analyzing the light may also include forming the light into an image of the illuminated tissue. The image of the illuminated tissue may be projected onto the eyes of a surgeon or sensed by a matrix of light detectors disposed on a jaw member of the tissue-sealing instrument and transmitted to a display.

16 Claims, 5 Drawing Sheets

(51) Int. Cl.
| | |
|---|---|
| *A61B 90/30* | (2016.01) |
| *A61B 18/00* | (2006.01) |
| *A61N 7/00* | (2006.01) |
| *A61B 1/00* | (2006.01) |
| *A61B 5/00* | (2006.01) |
| *A61B 17/28* | (2006.01) |
| *A61B 17/00* | (2006.01) |
| *A61B 90/00* | (2016.01) |

(52) U.S. Cl.
CPC ......... *A61B 5/0071* (2013.01); *A61B 5/0084* (2013.01); *A61B 17/2812* (2013.01); *A61B 2017/00057* (2013.01); *A61B 2017/00061* (2013.01); *A61B 2018/0063* (2013.01); *A61B 2018/00404* (2013.01); *A61B 2018/00589* (2013.01); *A61B 2018/00595* (2013.01); *A61B 2018/00607* (2013.01); *A61B 2018/00702* (2013.01); *A61B 2018/00726* (2013.01); *A61B 2018/00732* (2013.01); *A61B 2018/00791* (2013.01); *A61B 2018/00827* (2013.01); *A61B 2018/00875* (2013.01); *A61B 2018/00892* (2013.01); *A61B 2018/00982* (2013.01); *A61B 2090/3941* (2016.02); *A61B 2562/0238* (2013.01); *A61B 2562/046* (2013.01); *A61N 2007/0017* (2013.01)

(58) Field of Classification Search
CPC ......... A61B 2018/00892; A61B 2018/00875; A61B 2018/00827; A61B 2018/00791; A61B 2018/00732; A61B 2018/00726; A61B 2562/046; A61B 2018/0063
See application file for complete search history.

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | Decarolis | |
| 5,147,356 A | 9/1992 | Bhatta | |
| D343,453 S | 1/1994 | Noda | |
| D348,930 S | 7/1994 | Olson | |
| D349,341 S | 8/1994 | Lichtman et al. | |
| 5,336,221 A | 8/1994 | Anderson | |
| D354,564 S | 1/1995 | Medema | |
| D358,887 S | 5/1995 | Feinberg | |
| 5,470,331 A | 11/1995 | Daikuzono | |
| D384,413 S | 9/1997 | Zlock et al. | |
| H1745 H | 4/1998 | Paraschac | |
| 5,762,609 A | 6/1998 | Benaron et al. | |
| 5,769,791 A * | 6/1998 | Benaron ............ | A61B 5/0084 600/473 |
| 5,772,597 A * | 6/1998 | Goldberger et al. ......... | 600/473 |
| D402,028 S | 12/1998 | Grimm et al. | |
| D408,018 S | 4/1999 | McNaughton | |
| D416,089 S | 11/1999 | Barton et al. | |
| 6,039,729 A | 3/2000 | Durville et al. | |
| D424,694 S | 5/2000 | Tetzlaff et al. | |
| D425,201 S | 5/2000 | Tetzlaff et al. | |
| 6,086,586 A | 7/2000 | Hooven | |
| H1904 H | 10/2000 | Yates et al. | |
| 6,248,117 B1 | 6/2001 | Blatter | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,611,320 B1 * | 8/2003 | Lindberg ........... | A61B 5/14551 356/40 |
| 6,623,494 B1 | 9/2003 | Blatter | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| 7,217,266 B2 | 5/2007 | Anderson et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,684,846 B2 | 3/2010 | Johnson et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2004/0106880 A1 * | 6/2004 | Weng ................. | A61B 8/4422 601/2 |
| 2004/0176752 A1 | 9/2004 | Alfano et al. | |
| 2005/0234437 A1 | 10/2005 | Baxter et al. | |
| 2006/0173355 A1 * | 8/2006 | Alfano et al. ............... | 600/476 |
| 2006/0258629 A1 * | 11/2006 | Freeman ..................... | 514/150 |
| 2007/0032723 A1 * | 2/2007 | Glossop ................ | A61B 1/018 600/424 |
| 2007/0038209 A1 | 2/2007 | Buysse et al. | |
| 2007/0179484 A1 | 8/2007 | Sade | |
| 2007/0260231 A1 * | 11/2007 | Rose ..................... | A61B 18/22 606/13 |
| 2008/0009860 A1 | 1/2008 | Odom | |
| 2008/0221409 A1 | 9/2008 | Hoarau | |
| 2009/0024034 A1 * | 1/2009 | Moreau-Gobard ......... | A61B 8/4227 600/443 |
| 2009/0287194 A1 | 11/2009 | Gertz et al. | |
| 2009/0322907 A1 * | 12/2009 | Takahashi .......... | A61B 1/00004 348/234 |
| 2010/0049187 A1 | 2/2010 | Carlton et al. | |
| 2010/0160791 A1 | 6/2010 | Liu et al. | |
| 2010/0160904 A1 | 6/2010 | McMillan et al. | |
| 2010/0217258 A1 | 8/2010 | Floume et al. | |
| 2010/0274178 A1 * | 10/2010 | LePivert ......................... | 604/21 |
| 2011/0098531 A1 * | 4/2011 | To ...................... | A61B 17/1671 600/114 |
| 2011/0125165 A1 * | 5/2011 | Simaan ................. | A61F 9/007 606/130 |
| 2011/0160570 A1 * | 6/2011 | Kariv ..................... | A61B 5/721 600/424 |
| 2012/0078117 A1 * | 3/2012 | Okada ................ | A61B 5/0075 600/476 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |

(56) References Cited

FOREIGN PATENT DOCUMENTS

| | | |
|---|---|---|
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 0480293 A1 | 4/1992 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 05/110264 | 11/2005 |
| WO | WO2009005850 * | 1/2009 |
| WO | WO 2009005850 A1 * | 1/2009 |

OTHER PUBLICATIONS

U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glennn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.

(56) References Cited

OTHER PUBLICATIONS

U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.

(56) References Cited

OTHER PUBLICATIONS

Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/USO4/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report PCT/US2012/038112, dated Jul. 16, 2012.
International Search Report PCT/US2012/038126, dated Jul. 16, 2012.
European Office Action for EP 12724795 dated Jul. 27, 2015.
Examination Report issued in corresponding EP Patent Application No. 12724795.5 dated May 30, 2016, 5 pages.

\* cited by examiner

OPTICAL RECOGNITION OF TISSUE AND VESSELS

BACKGROUND

1. Technical Field

The present disclosure relates to methods and apparatus for recognizing tissue parameters during a surgical procedure, and more particularly to methods and apparatus of energy-based tissue sealing that employ optical components for recognizing tissue parameters.

2. Background of Related Art

Existing energy-based tissue-sealing devices use different types of energy to heat tissue. The different types of energy used to heat tissue include direct heat conduction from a heating element (see, e.g., U.S. Pat. No. 6,220,346), RF current (see, e.g., U.S. Pat. No. 7,384,420), and ultrasound (see, e.g., U.S. Publication No. 2007/10179379). A typical energy-based tissue-sealing device includes jaw members for grasping and compressing the tissue and applying energy to the tissue.

During a surgical procedure, it is important for a surgeon to be able to determine the exact location of and the type of structures within tissue. For example, when performing a tissue-sealing procedure, it is important for a surgeon to be able to determine the exact location of and the type of vessel within tissue. This information allows a surgeon to correctly position the jaw members of a tissue-sealing instrument with respect to the vessel so that the surgeon can create a high-quality tissue seal. Correctly positioning the tissue-sealing instrument is especially important during laparoscopic operations when the surgeon's field of view may be limited.

Existing tissue-sealing instruments may not provide sufficient information about the location of vessels within tissue or other information about the vessels within tissue. Also, typical tissue-sealing instrument designs include jaw members that are not transparent. As a result, the jaw members tend to block or obscure the surgeon's view of tissue grasped by the jaw members.

SUMMARY

The method and apparatus of the present disclosure enables a surgeon to view or recognize tissue parameters while manipulating the tissue with a surgical instrument during a surgical procedure. In one aspect, the present disclosure features a method of recognizing tissue during an energy-based tissue-sealing procedure. The method includes grasping tissue with an energy-based tissue-sealing instrument, illuminating the grasped tissue or tissue adjacent to the grasped tissue with light, forming a spatial distribution of the light transmitted, scattered, or reflected by the tissue into an image of the tissue, and recognizing the tissue based on the image of the tissue.

The method may further include analyzing a spectral distribution of the light transmitted, scattered, or reflected by the tissue, and recognizing the tissue based on the result of analyzing the spectral distribution of the light transmitted, scattered, or reflected by the tissue.

In some embodiments, illuminating the tissue with light includes illuminating the tissue with light having a wavelength selected so that the difference between the absorption or scattering of the light by the vessel and the absorption or scattering of the light by tissue surrounding the vessel is sufficient for recognizing the vessel based on the light transmitted, scattered, or reflected by the tissue. In other embodiments, illuminating the tissue with light includes illuminating the tissue with light having at least a first wavelength and a second wavelength. The first wavelength is selected so that the difference between absorption or scattering of the light of the first wavelength by the vessel and absorption or scattering of the light of the first wavelength by tissue surrounding the vessel is sufficient to recognize the vessel based on the light transmitted, scattered, or reflected by the tissue. The second wavelength is selected so that the magnitude of the absorption or scattering of the light of the second wavelength by the vessel is approximately equal to the magnitude of the absorption or scattering of the light of the second wavelength by the tissue surrounding the vessel.

The method may further include correlating the light of the first wavelength transmitted, scattered, or reflected by the tissue with the light of the second wavelength transmitted, scattered, or reflected by the tissue to determine a position of the vessel in the tissue surrounding the vessel. In some embodiments, grasping tissue includes applying time-varying force to the tissue to vary the amount of fluid in the vessel.

The method may further include introducing a marker into fluid flowing in the vessel. The marker may be a luminescent marker. The method may also include analyzing luminescent light emitted from the marker to determine a parameter of the vessel. The parameter of the vessel includes a size of the vessel, further comprising generating an alarm signal when the size of the vessel reaches a predetermined size.

In some embodiments, illuminating the tissue with light includes illuminating the tissue with light having a wavelength selected so that the difference between the absorption or scattering of the light by the marker and the absorption or scattering of the light by the tissue is sufficient to distinguish between the marker and the tissue. In other embodiments, illuminating the tissue with light includes illuminating the tissue with light having at least one wavelength absorbable by the marker to cause the marker to emit luminescent light. In yet other embodiments, illuminating the tissue with light includes illuminating the tissue with light having at least a first wavelength and a second wavelength. The first wavelength is selected so that the difference between the absorption or scattering of the light of the first wavelength by the marker and the absorption or scattering of the light of the first wavelength by the tissue is sufficient to distinguish between the marker and the tissue in the light transmitted, scattered, or reflected by the tissue. The second wavelength is selected so that the magnitude of absorption or scattering of the light of the second wavelength by the marker and the magnitude of absorption or scattering of the light of the second wavelength by the tissue are substantially equal.

The method may further include correlating the light of the first wavelength transmitted, scattered, or reflected by the tissue with the light of the second wavelength transmitted, scattered, or reflected by the tissue, and determining the position of the vessel in tissue surrounding the vessel based on the result of correlating the light of the first wavelength transmitted, scattered, or reflected by the tissue with the light of the second wavelength transmitted, scattered, or reflected by the tissue.

In another aspect, the present disclosure features an energy-based tissue-sealing instrument. The energy-based tissue-sealing instrument includes a first jaw member made of a transparent or semitransparent material, a second jaw member disposed opposite the first jaw member, a transparent or semi-transparent contact coupled to the first jaw member, and an optical system coupled to the second jaw member. The first jaw member and the second jaw member are operable to move in opposite directions to grasp tissue. Also, the first jaw member is configured to transmit the light transmitted or scattered by the tissue to an exterior surface of the first jaw member. The transparent or semi-transparent contact is configured to apply energy to the tissue to seal the tissue. The optical system is configured to illuminate tissue with a light beam.

The optical system may include a light source configured to generate light and a beam former configured to form the light into the light beam and to illuminate the tissue with the light beam. Also, the energy-based tissue-sealing instrument may further include a second transparent or semi-transparent contact coupled to the second jaw member. The second transparent or semi-transparent contact is configured to apply energy to the tissue to seal the tissue. Also, the optical system may be disposed between the second transparent or semi-transparent contact and at least a portion of the second jaw member.

The energy-based tissue-sealing instrument may further include an optical sensor coupled to the exterior surface of the first jaw member. The optical sensor is configured to sense the light transmitted to the exterior surface of the first jaw member. The optical sensor may include a matrix of optical detectors.

In some embodiments, the first jaw member is further configured to project the light transmitted or scattered by the tissue onto at least one eye of a user of the energy-based tissue-sealing instrument. For example, the first jaw member may include a lens configured to project the light transmitted or scattered by the tissue onto at least one eye of a user of the energy-based tissue-sealing instrument.

BRIEF DESCRIPTION OF THE DRAWINGS

The system and method of optical recognition of tissues and vessels will now be described with reference to the accompanying drawings.

DETAILED DESCRIPTION

The method and apparatus of the present disclosure helps a surgeon to view and recognize tissue parameters while the tissue is grasped by a surgical instrument. The method includes the steps of grasping tissue with an energy-based surgical instrument, illuminating the grasped tissue with light, and analyzing the light that is transmitted and/or scattered by the tissue. The transmitted and/or scattered light is analyzed to determine parameters associated with the tissue or any vessels disposed within the tissue.

The transmitted and/or scattered light may indicate whether there is a vessel located within a volume of tissue. The light may also indicate the spatial distribution of vessels within a volume of tissue. The light may further indicate the type of tissue or the type of vessel within tissue. A surgeon can use all or a portion of this information to more accurately position the tissue-sealing instrument and achieve a high-quality tissue seal and cut.

Figure 1:
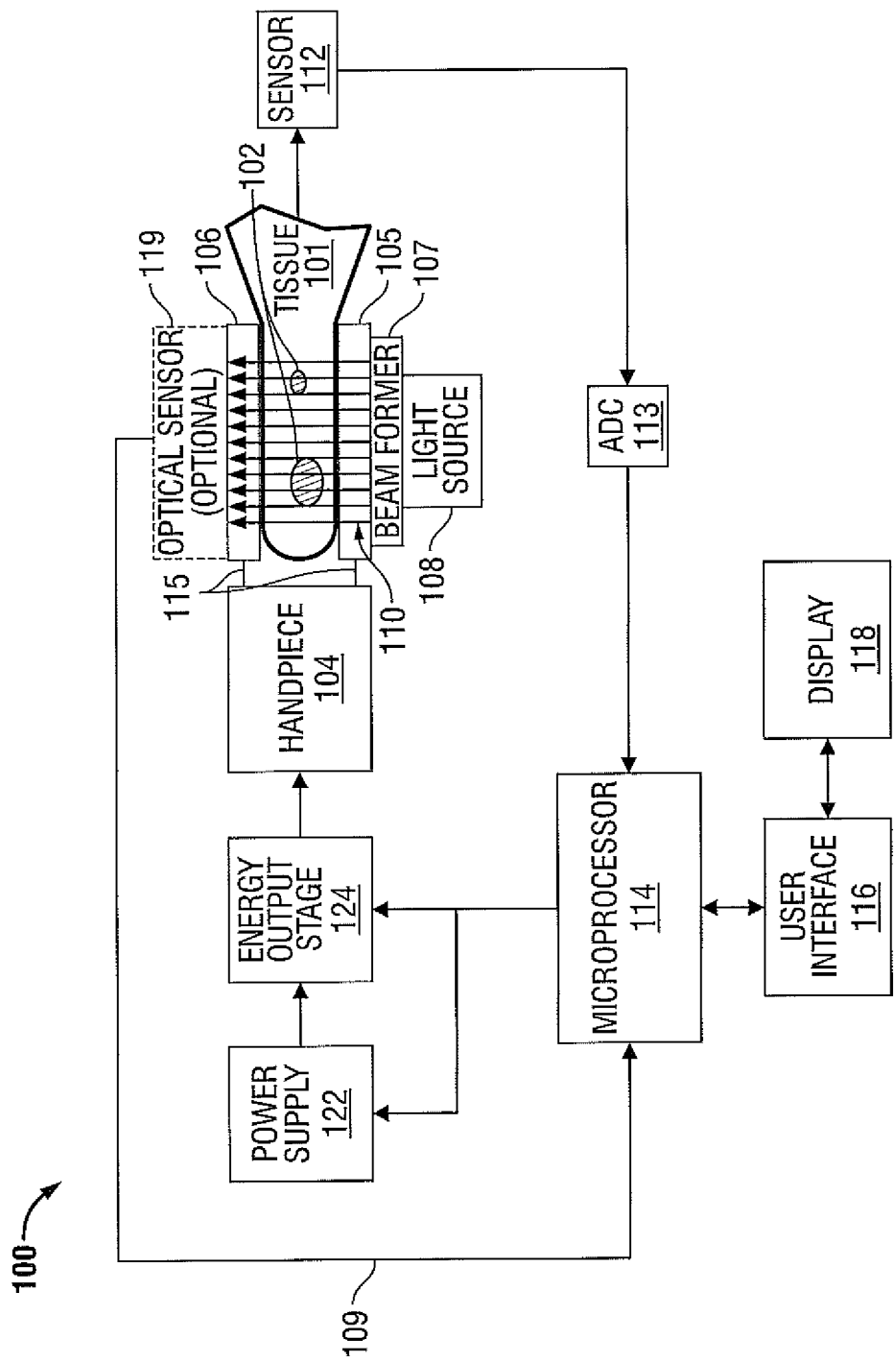
FIG. 1 is a block diagram of a tissue-sealing system including optical components for detecting tissue parameters according to embodiments of the present disclosure.

FIG. 1 illustrates an energy-based tissue-sealing system 100 according to embodiments of the present disclosure. The energy-based tissue-sealing system 100 (and the methods described below) may use any type of energy to seal tissue including mechanical energy, acoustical energy, thermal energy, electric energy, or electromagnetic energy (e.g., optical energy or radio frequency (RF) energy).

The energy-based tissue-sealing system 100 includes a power supply 122, an energy output stage 124, and an energy-based instrument having a handpiece 104 and transparent contacts 105, 106. The power supply 122 provides power to the energy output stage 124, which, in turn, provides energy to the tissue 101 via the handpiece 104 and the transparent contacts 105, 106. For an RF-based tissue-sealing system, the energy output stage 124 provides RF energy to the tissue 101 via at least one contact 105, 106 of the energy-based instrument 126 to seal the tissue 101.

The tissue-sealing system 100 also includes a sensor 112, an analog-to-digital converter (ADC) 113, a microprocessor 114, a user interface 116, and a display 118. The sensor 112 senses various parameters or properties of tissue 101 at the operating site and transmits analog sensor signals representing the sensed parameters or properties of the tissue 101 to the ADC 113. The ADC 113 converts the analog sensor signals into digital sensor data and transmits the digital sensor data to the microprocessor 114. The microprocessor 114 processes the digital sensor data and generates control signals based on the processed digital sensor data to control the power supply 122 and/or the energy output stage 124. For example, the microprocessor 114 may regulate the voltage or current output from the power supply 122 or the energy output stage 124 based on the processed digital sensor data.

The sensor 112 may be configured to measure or sense various electrical or electromechanical conditions at the operating site such as tissue impedance, changes in tissue impedance, tissue temperature, changes in tissue temperature, leakage current, applied voltage, and applied current. The sensor 112 continuously measures one or more of these conditions so that the microprocessor 114 can continually adjust the energy output from the power supply 122 and/or the energy output stage 124.

The user interface 116 is coupled to the microprocessor 114 allowing a user to control various parameters of the energy applied to the tissue 101 during a surgical procedure. For example, the user interface 116 may allow a user to manually set, regulate and/or control one or more parameters of the energy delivered to the tissue, such as voltage, current, power, frequency, and/or pulse parameters, e.g., pulse width, duty cycle, crest factor, and/or repetition rate.

The microprocessor 114 is capable of executing software instructions for processing data received from the user interface 116 and the ADC 113 and for outputting control signals to the power supply 122 and/or the energy output stage 124. The software instructions are stored in an internal memory of the microprocessor 114, an internal or external memory bank accessible by the microprocessor 114 and/or an external memory, e.g., an external hard drive, floppy diskette, or CD-ROM. Control signals generated by the microprocessor 114 may be converted to analog signals by a digital-to-analog converter (DAC) (not shown) before being applied to the power supply 122 and/or energy output stage 124.

For an RF-based tissue-sealing system, the power supply 122 may be a high-voltage DC power supply that produces RF current. The microprocessor 114 generates control signals to control the magnitude of the voltage and current output by the DC power supply 122. The energy output stage 124 receives the output current from the DC power supply 122 and generates one or more pulses via a waveform generator (not shown). The microprocessor 114 generates control signals to regulate the pulse parameters, such as pulse width, duty cycle, crest factor, and repetition rate. In other embodiments, the power supply 122 may be an AC power supply, and the energy output stage 124 may vary the waveform of the signal provided by the power supply 122 to achieve a desired waveform.

The user interface 116 may be local to or remote from the microprocessor 114. A user may enter data, such as the type of instrument, the type of procedure, and/or the type of tissue. Furthermore, the user may enter commands, such as a target effective voltage, current or power level. The user may also enter commands for controlling parameters of the energy that is delivered from the energy output stage 124 to the handpiece 104 and the contacts 105, 106.

The energy-based tissue-sealing system 100 also includes an optical system for allowing a surgeon to view parameters of the tissue 101 and the vessels 102 within the tissue 101. The optical system includes a light source 108, a beam former 107, transparent contacts 105, 106, and an optional optical sensor 119. The light source 108 supplies light to a beam former 107, which forms the light into a light beam 110. The light beam 110 propagates through the first transparent contact 105, the tissue 101, and the second transparent contact 106. The optical sensor 119 senses the light beam transmitted through the tissue 101 and provides optical sensor signals to the microprocessor 114 via the communications link 109. The optical sensor 119 may include a matrix of detectors as described in more detail below. The microprocessor 114 analyzes the optical sensor signals to determine parameters of the tissue 101 and/or the vessel 102. The microprocessor 114 also processes the optical sensor signals and transmits the processed optical sensor signals to the display 118 so that a user may view a transparency image of the vessels 102 within the tissue 101.

In other embodiments, the tissue-sealing system 100 may not include the optical sensor 119. In this instance, the light beam 110 is simply transmitted through the contacts 105, 106 and the tissue 101 and projected onto a surgeon's eyes 210. Accordingly, the surgeon can view a transparency image of the vessels 102 or other parameters associated with the tissue 101 or the vessels 102. By viewing the transparency image, the surgeon can recognize or identify the type of the tissue 101 or the vessels 102 within the tissue 101. The surgeon can also monitor the tissue 101 or the vessels 102 within the tissue 101 while performing a surgical procedure.

Figure 2:
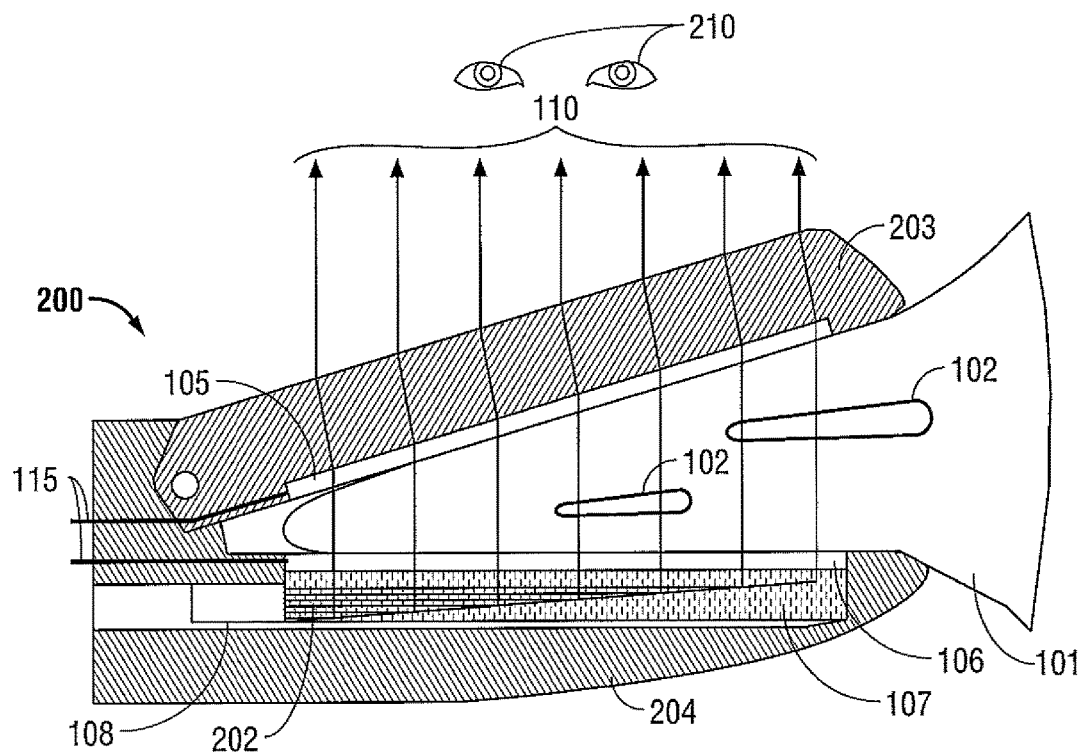
FIG. 2 is a cross-sectional side view of a portion of a tissue-sealing instrument including optical components for detecting tissue parameters according to some embodiments of the present disclosure.

FIG. 2 is a cross-sectional side view of a portion of an RF-based tissue-sealing instrument 200 that may be used in the tissue sealing system of FIG. 1. The RF-based tissue-sealing instrument 200 includes an upper jaw member 203 and a lower jaw member 204 that are mechanically coupled together (e.g., by a hinge) so that the upper jaw member 203 can move with respect to the lower jaw member 204 and the jaw members 203, 204 can grasp the tissue 101. The upper jaw member 203 is made of a material that is optically transparent or semi-transparent to light having a particular wavelength or a spectrum of wavelengths. The upper jaw member 203 includes an optically transparent or semi-transparent contact plate 105. Similarly, the lower jaw member 204 includes an optically transparent or semi-transparent contact plate 106.

The beam former 107 is disposed beneath the contact plate 106 in the lower jaw member 204. The light 202 generated by the light source 108 propagates into the beam former 107, which forms the light 202 into a light beam 110. The beam former 107 projects the light beam 110 onto the tissue 101 through the transparent or semi-transparent contact plate 106. The beam former 107 may include different optical refracting, reflecting, and guiding components to guide the light from the light source and to form the light beam 110. For example, the beam former 107 may include optical fibers and prisms as disclosed in commonly-owned U.S. patent application Ser. No. 12/757,340, entitled "Optical Hydrology Arrays and System and Method for Monitoring Water Displacement During Treatment of Patient Tissue," the entire contents of which are incorporated by reference herein.

In other embodiments, the beam former 107 may form the light 202 into a light spot that is smaller than the light beam 110. In such embodiments, the beam former 107 may include optical components configured to scan the tissue 101 with the light spot.

The light beam 110 is transmitted through the tissue 101 and is selectively absorbed and/or scattered by vessels 102 and by the surrounding tissue. After passing through the tissue 101, the light beam 110 passes through the transparent or semitransparent contact plate 105 and the upper jaw member 203 to the surgeon's eyes 210.

Luminescent markers may be introduced into the tissue 101 or the vessels 102 to highlight a parameter of the tissue 101 or to increase the contrast between the tissue 101 and the vessels 101. The upper jaw member 203 may be made of a material that is optically transparent at the wavelength of the luminescent light to allow the luminescent light to pass through the upper jaw member 203. The upper jaw member 203 may be configured to form the luminescent light into an image and to project the image onto the surgeon's eyes 210 so that the surgeon can view, among other parameters, the positions of the vessels 102 within the tissue 101.

During a surgical procedure, the tissue 101 is grasped between the jaw members 203, 204 and RF energy is applied to the grasped tissue 101 through the contact plates 105, 106. Contact plates 105, 106 are formed of a material that is optically transparent or semi-transparent at the wavelength of the light beam 110. If luminescent markers are introduced into tissue 101 or the vessels 102, the contact plate material may also be made optically transparent or semi-transparent at the wavelength of luminescent light. The transparent contact plates 105, 106 can be fabricated, for example, by depositing Indium Tin Oxide on a transparent dielectric substrate. Alternatively, the contact plates 105, 106 can be made semi-transparent, for example, by depositing a conducting metal mesh or grid on a transparent dielectric substrate. Contact plates 105, 106 are electrically coupled to the energy output stage 124 of FIG. 1 via electrical conductors or leads 115.

In some embodiments, additional optical elements can be placed on the outer surface of the transparent upper jaw member 203 to modify the image that is projected onto the surgeon's eyes 210. For example, lenses can be disposed on the outer surface of the transparent upper jaw member 203 to form an image that meets the needs of the surgeon during a surgical procedure. In other embodiments, the jaw member 203 may be shaped so as to modify the light beam 110. For example, the outer surface of the jaw member 203 may have a concave or convex shape to modify the transmitted light 110 in a way that provides more convenient conditions for the surgeon to observe the image created by the transmitted light 110.

Grasping tissue with the surgical instrument 200 creates favorable conditions for viewing tissue structures and parameters of those structures, such as the density of vessels 102 within tissue 101. When tissue 101 is grasped with the surgical instrument 200, the jaw members 203, 204 may move towards each other and apply an appropriate amount of pressure on the tissue to leave a sufficient amount of biological fluid within the vessels 102 to achieve the best image quality. The applied pressure may be less than that used for a tissue-sealing procedure. The applied pressure may also be varied during a vessel recognition procedure to provide variations in the amount of biological fluid within the vessels 102. These variations cause variations in the vessel image intensity, which can improve the recognition of vessels 102 or other parameters of the tissue 101 relative to surrounding tissue.

When there is a difference in absorption and/or scattering spectra between the vessel 102 (including vessel walls and vessel content) and surrounding tissue, the wavelength of the light beam 110 may be selected from that part of the spectrum where the difference in absorption and/or scattering spectra between the vessel 102 and surrounding tissue is relatively high or at least sufficient to distinguish the vessel 102 from the surrounding tissue.

The optical contrast between the images of tissue structures, e.g., between the vessels 102 and the tissue 101 surrounding the vessels 102, and the level of detail of the images depends on the optical properties of the tissue 101 and vessels 102. For some tissues, the optical contrast between the images of tissue structures may not be enough. For example, the difference between absorption and/or scattering of the light by the vessel 102 and absorption and/or scattering of the light by the tissue 101 surrounding the vessel 102 may not be enough to detect a vessel in a transparency image of the tissue. To increase the optical contrast between the images of the vessels 102 and the tissue 101 surrounding the vessels 102, a marker can be added to the biological fluid circulating or flowing through the vessels 102. The marker may be a substance that has high optical absorption and/or luminescent properties.

In some embodiments, the marker substance is selected to have a predetermined absorption, scattering, or luminescence spectrum that is different from the absorption spectrum of the tissue surrounding the vessel so that the marker substance can be detected in the light transmitted, scattered, or reflected by the tissue. For example, a marker substance may be introduced into the cholecystis to facilitate the detection of bile ducts in tissue surrounding the bile ducts. The marker substance may include a fluorescence agent. Some examples of vascular fluorescence agents are PerkinElmer Inc.'s Genhance™ 680 and Genhance™ 750.

Figure 3:
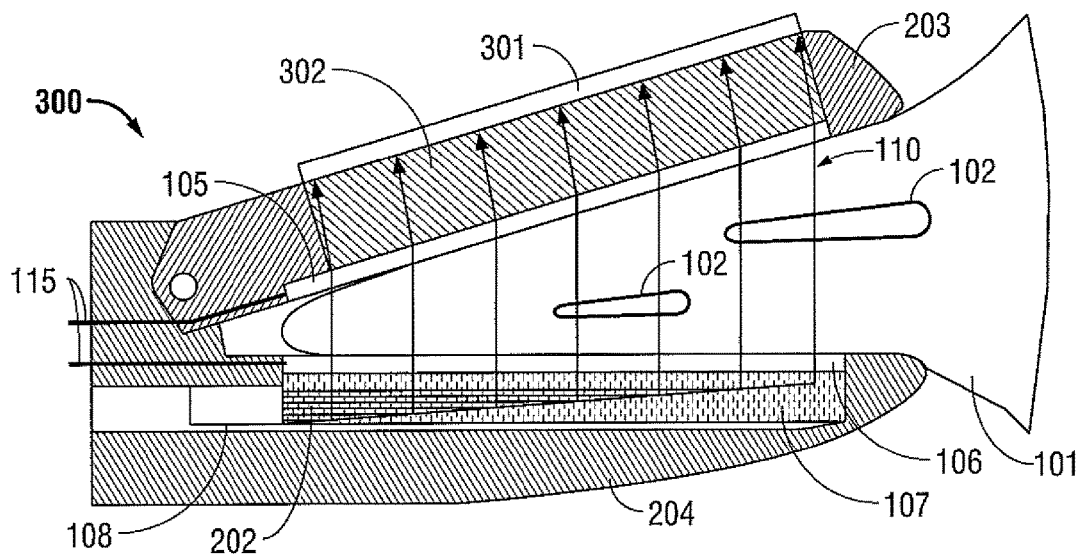
FIG. 3 is a cross-sectional side view of a portion of a tissue-sealing instrument using a matrix of photo detectors to sense the transparency image of the tissue according to other embodiments of the present disclosure.

FIG. 3 illustrates a portion of an instrument 300 that includes a light detector matrix 301 (e.g., a CCD matrix) for detecting the transparency image of tissue 101. The light detector matrix 301 is disposed on the outer surface of the upper jaw member 203. An optical element 302 may be disposed between the detector matrix 301 and the transparent contact plate 106 to transform the light 110, which is transmitted through the tissue 101, to form a detectable distribution of light at the detector matrix 301. In some embodiments, the optical element 302 is a bundle of optical fibers. In other embodiments, the optical element 302 is a lens. The detector matrix 301 detects the distribution of the light beam 110 and transmits a detection signal to the microprocessor 114 of FIG. 1 via the communications link 109. The microprocessor 114 processes the detection signal to obtain an image, which is transmitted to a display 118 via user interface 116 so that a user can view the image.

The display 118 may include a camera monitor used in laparoscopic surgical procedures. Accordingly, a surgeon can have a clear and unobstructed view of the surgical site even while using a surgical instrument during a laparoscopic surgical procedure. In some embodiments, a detector matrix similar to detector matrix 301 is positioned in the lower jaw member 204 to obtain an image of the vessels 102 based on light reflected or scattered from the tissue 101. For example, the detector matrix may be positioned between the contact plate 106 and the beam former 107.

To prevent tissue thickness variations and other tissue structure inhomogeneities from distorting or otherwise influencing the image, the light source 108 and/or the beam former 107 can generate two or more wavelengths of light. One of the wavelengths can be selected from that part of the electromagnetic spectrum where the difference between the magnitude of absorption and/or scattering of light by the vessel 102 and the magnitude of absorption and/or scattering of light by the surrounding tissue is large. The other wavelength(s) can be selected from that part of the electromagnetic spectrum where the difference between the magnitude of absorption and/or scattering of light by the vessel 102 and the magnitude of absorption and/or scattering of light by the surrounding tissue is small. For example, the light source 108 may include two light sources (e.g., LEDs) that generate light at two different wavelengths of about 530 nm (green) and 630 nm (red). Accordingly, the detector matrix 301 can detect multiple transparency images of the tissue 101 for different wavelengths.

The detector matrix 301 may transmit the multiple images of the tissue 101 to the microprocessor 114, which may process the transparency images to find the correlation between them. This correlation information may be used, for example, to determine the position of a vessel 102 in the surrounding tissue. The microprocessor 114 may use any one of a number of image processing techniques known to those skilled in the art for finding the correlation between the transparency images. The correlation analysis of the transparency images may exclude intensity variations related to varying tissue thickness and other inhomogeneities of the tissue structure that are unrelated to the vessels to be identified.

Figure 4:
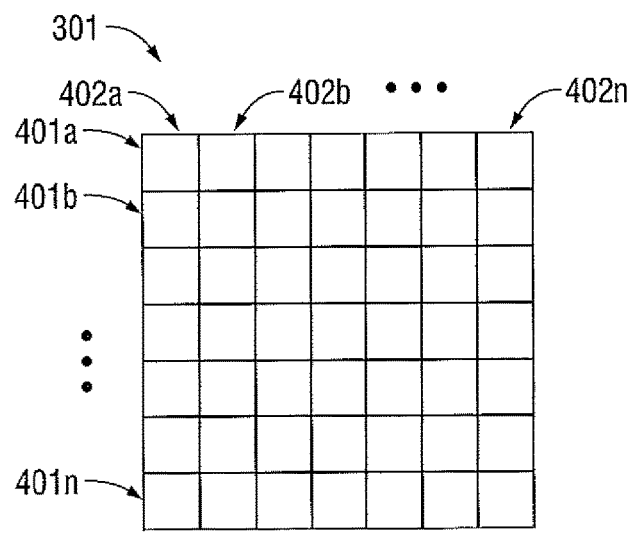
FIG. 4 is a diagram of the matrix of optical detectors used in the tissue-sealing instrument of FIG. 3 according to embodiments of the present disclosure.

FIG. 4 is a diagram of the detector matrix 301 used in the tissue-sealing instrument of FIG. 3 according to certain embodiments of the present disclosure. The detector matrix 301 includes multiple rows 401a-401n and multiple columns 402a-402n of optical detectors. Each optical detector in the detector matrix 301 (e.g., the optical detector located in row 401a and column 402b) is configured to detect one or more parameters (e.g., intensity, polarization, and frequency spectrum) of a portion of the light beam 110. The parameters of each portion of the light beam 110 that are detected by the detector matrix 301 are then transmitted to the microprocessor 114 for analysis (e.g., spectral analysis) and processing.

Figure 5:
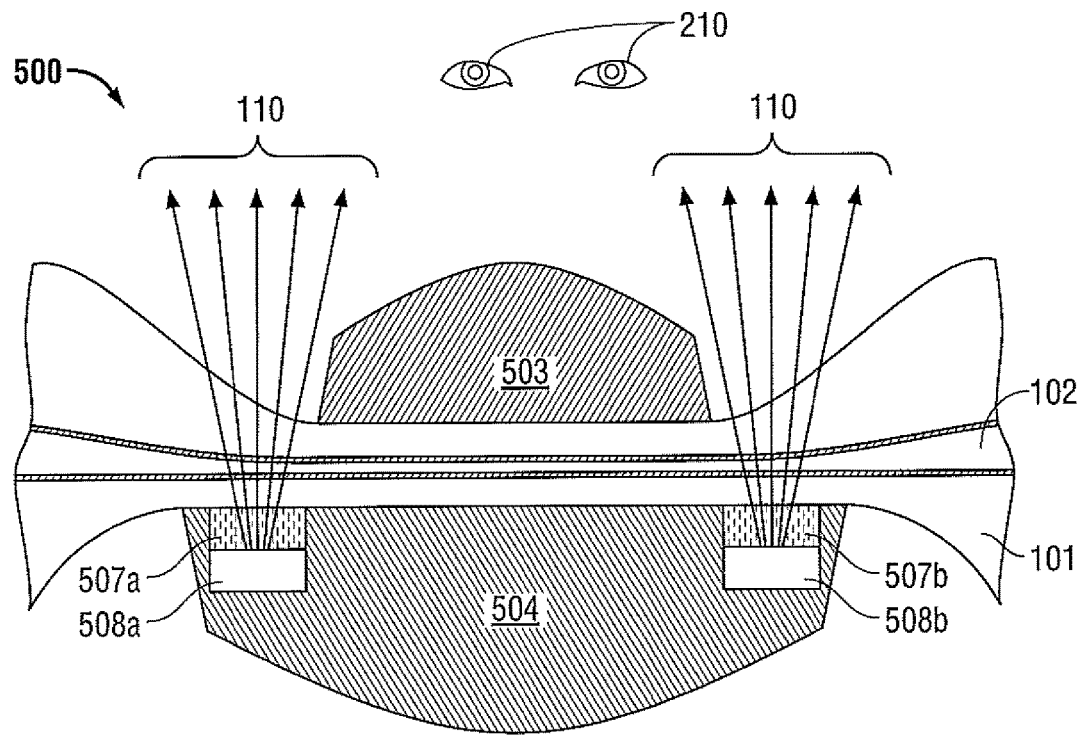
FIG. 5 is a cross-sectional front view of a tissue-sealing instrument without optically transparent jaw members according to yet other embodiments of the present disclosure.

FIG. 5 is a cross-sectional front view of an energy-based sealing instrument 500 that does not have optically transparent jaw members. The energy-based sealing system includes a lower jaw member 504 that is wider than the upper jaw member 503. Those portions of the lower jaw member 504 that extend outside of the footprint of the upper jaw member 503 each have a light source 508a, 508b and a corresponding beam former 507a, 507b. In other embodiments, the lower jaw member 504 may extend beyond only one side of the footprint of the upper jaw member 503, in which case the lower jaw member 504 would include a single light source and corresponding beam former.

The light beams 110 produced by the light sources 508a, 508b and the beam formers 507a, 507b illuminate those portions of tissue near the edges of the upper jaw member 503. As a result, the light beams 110 that are transmitted and/or scattered by that portion of the tissue 101 and vessel 102 that is adjacent to the tissue 101 and vessel 102 grasped by the jaw members 503, 504 can be directly observed by a surgeon.

In other embodiments, the light sources 508a, 508b, the beam formers 507a, 507b, and the other components needed to view or to detect a transparency image of the tissue 101 and vessel 102 may be disposed on an instrument or probe that is separate from the tissue-sealing instrument. The separate instrument or probe may fit around the tissue-sealing instrument. Alternatively, the separate instrument or probe may be a standalone instrument or probe that may be used together with the tissue-sealing instrument.

Embodiments of the present disclosure may employ different types of energy or combinations of different types of energy to create an image of the tissue 101 and vessel 102 and to recognize parameters of the tissue 101 and vessel 102. For example, light in the visible light spectra may be used together with ultrasonic energy to recognize a tissue structure. As another example, electromagnetic energy outside of the visible light range, such as in the Terahertz range, may be used with an appropriate detector to recognize a particular tissue structure.

Figure 6:
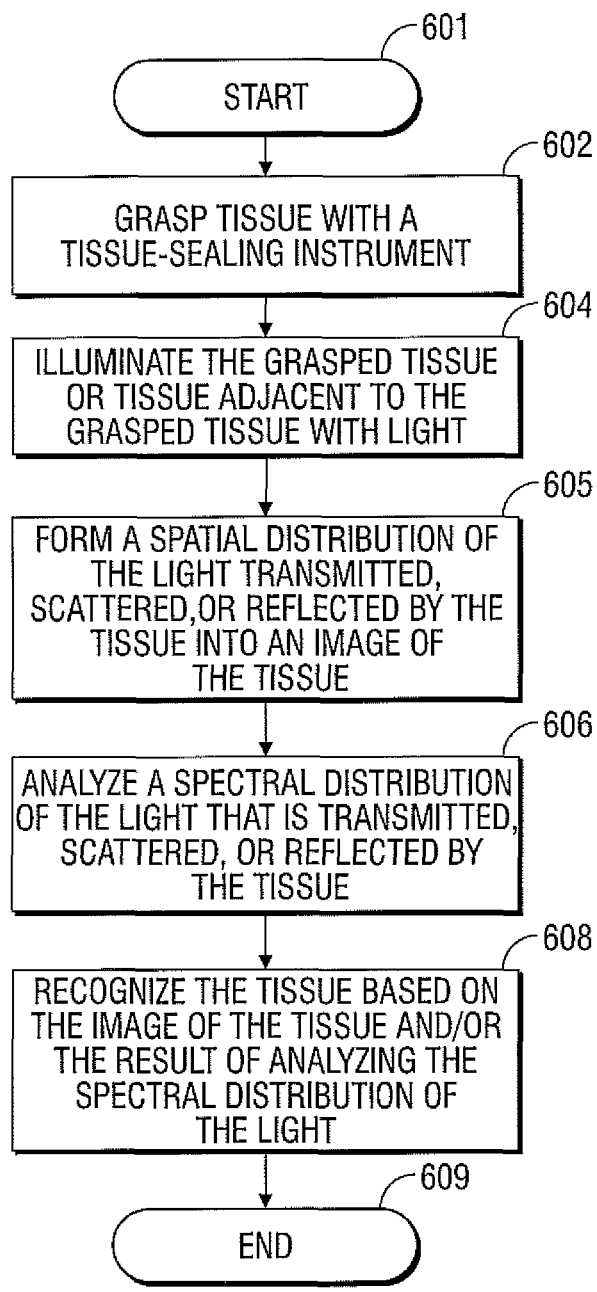
FIGS. 6 and 7 are flow diagrams of methods for recognizing tissue during a tissue-sealing procedure according to embodiments of the present disclosure.

FIG. 6 is a flow diagram of a method for recognizing tissue during a tissue-sealing procedure. After starting in step 601, tissue is grasped with a tissue-sealing instrument, in step 602. Then, in step 604, the grasped tissue or tissue adjacent to the grasped tissue is illuminated with light. In step 605, a spatial distribution of the light that is transmitted, scattered, and/or reflected by the tissue is formed into an image of the tissue. Also, in step 606, a spectral distribution of the light that is transmitted, scattered, and/or reflected by the tissue is analyzed. Finally, before the process ends in step 609, the tissue is recognized based upon the image of the tissue and/or the result of analyzing the spectral distribution of the light in step 608.

In some embodiments, optical components of the tissue-sealing instrument or a separate instrument (1) form an image of the tissue based upon the light that is transmitted, scattered, or reflected by the tissue, and (2) project this image onto the surgeon's eyes 210. Accordingly, a surgeon can continually direct her eyes towards a surgical site within a surgical field of view without needing to redirect her eyes to a separate monitor or display located outside of the surgical field of view. For example, the surgeon can grasp tissue with a tissue sealing instrument and immediately see from the image of the tissue that a vessel is not properly positioned within the jaw members of the tissue-sealing instrument or that a vessel is not contained within the grasped tissue. In response, the surgeon can move the tissue-sealing instrument while visually tracking the vessel within the image of the tissue to properly position the jaw members with respect to the vessel.

Figure 7:
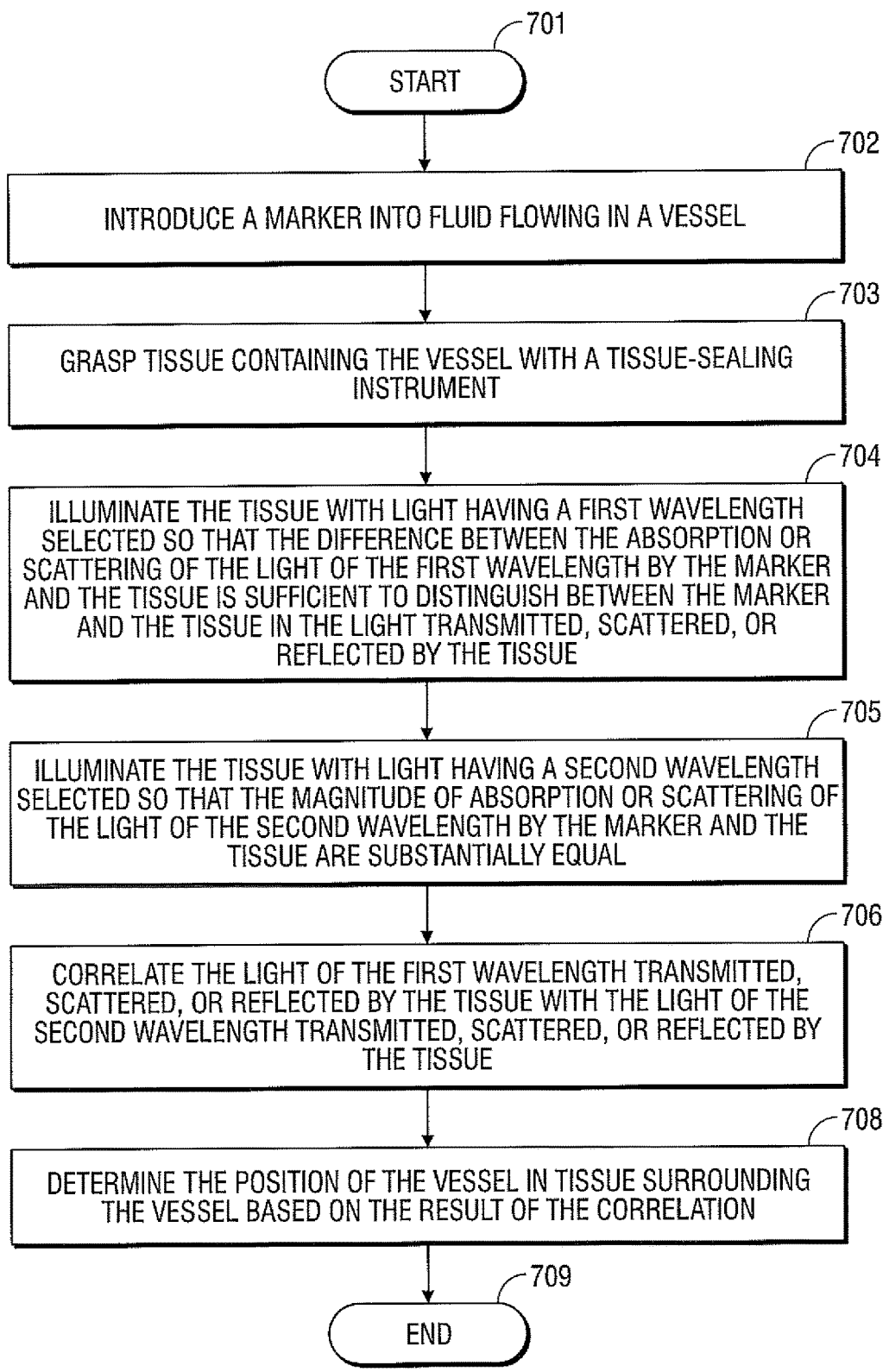

FIG. 7 is a flow diagram of another method for recognizing tissue during a tissue-sealing procedure according to other embodiments that use a marker to increase the optical contrast between vessels and surrounding tissue. After starting in step 701, a marker is introduced into fluid flowing in a vessel in step 702. In step 703, tissue containing the vessel is grasped with a tissue-sealing instrument. While the tissue is grasped with the tissue-sealing instrument, the tissue is illuminated with light having two different wavelengths. In particular, in step 704, the tissue is illuminated with light having a first wavelength selected so that the difference between the absorption or scattering of the light of the first wavelength by the marker and the tissue is sufficient to distinguish between the marker and the tissue in the light transmitted, scattered, or reflected by the tissue. In addition, in step 705, the tissue is illuminated with light having a second wavelength selected so that the magnitude of absorption or scattering of the light of the second wavelength by the marker and the tissue are substantially equal.

The tissue that is illuminated with light transmits, scatters, and/or reflects the light of the first and second wavelengths. In step 706, the light of the first wavelength and the light of the second wavelength that are transmitted, scattered, and/or reflected by the tissue are measured and correlated. Finally, in step 708, before the process ends in step 709, the position of the vessel within the tissue surrounding the vessel is determined based on the result of correlation.

In some embodiments, the spatial and spectral distribution of the light that is transmitted, scattered, and/or reflected by the tissue is analyzed and formed into an image of the illuminated tissue. For example, the optical sensor 119 of FIG. 1 may detect the spatial and spectral distribution of the light transmitted and/or scattered by the tissue and the microprocessor 114 may process this information and transmit a transparency image of the tissue to the user display 118. In another example, the transparent upper jaw member 203 of the tissue-sealing instrument 200 shown in FIG. 2 may be configured as a lens or other similar optical element to form an image of the illuminated tissue on the surgeon's eyes 210. In yet another example, the light may illuminate tissue adjacent to the tissue grasped by the tissue-sealing instrument as illustrated in FIG. 5. In this case, the light passes through the tissue and forms an image on the surgeon's eyes 210.

Although the present disclosure has been described with respect to particular embodiments, it will be readily apparent to those having ordinary skill in the art to which it appertains that changes and modifications may be made thereto without departing from the spirit or scope of the disclosure. For example, the energy-based tissue sealing system 100 of FIG. 1 may include circuitry and other hardware, rather than, or in combination with, programmable instructions executed by the microprocessor 114 for processing the digital sensor data and determining the control signals to transmit to the power supply 122 and the energy output stage 124.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

The invention claimed is:

1. A method of recognizing tissue during an energy-based tissue-sealing procedure, the method comprising:

grasping tissue, which includes a vessel, with an energy-based tissue-sealing instrument;

introducing a marker into fluid flowing in the vessel to increase contrast between the vessel and the tissue, wherein the marker is not introduced into the tissue;

selecting a first wavelength of light so that a difference between absorption or scattering of the light of the first wavelength by the marker and absorption or scattering of the light of the first wavelength by the tissue is sufficient to distinguish between the vessel and the tissue in the light transmitted, scattered, or reflected by the tissue;

selecting a second wavelength of light so that a difference between absorption or scattering of the light of the second wavelength by the marker and absorption or scattering of the light of the second wavelength by the tissue is not sufficient to distinguish between the vessel and the tissue in the light transmitted, scattered, or reflected by the tissue;

illuminating, by the energy-based tissue-sealing instrument, the grasped tissue or tissue adjacent to the grasped tissue with light having the first wavelength and the second wavelength;

forming a spatial distribution of the light transmitted, scattered, or reflected by the tissue into an image of the tissue;

projecting the image from the energy-based tissue-sealing instrument;

correlating light of the first wavelength transmitted, scattered, or reflected by the tissue with light of the second wavelength transmitted, scattered, or reflected by the tissue; and determining parameters of the tissue and a position of the vessel within the tissue based on the correlation between the light of the first wavelength and the light of the second wavelength.

2. The method of claim 1, further comprising:

analyzing a spectral distribution of the light transmitted, scattered, or reflected by the tissue and the marker; and recognizing the tissue based on a result of analyzing the spectral distribution of the light transmitted, scattered, or reflected by the tissue and the marker.

3. The method of claim 1, wherein grasping tissue includes applying time-varying force to the tissue to vary the amount of fluid in the vessel.

4. The method of claim 1, wherein illuminating the tissue with light includes illuminating the tissue with light having at least one wavelength absorbable by the marker to cause the marker to emit luminescent light.

5. The method of claim 1, wherein illuminating the tissue with light includes illuminating the tissue with light having at least a third wavelength and a fourth wavelength, the third wavelength selected so that the difference between absorption or scattering of the light of the third wavelength by the vessel and absorption or scattering of the light of the third wavelength by tissue surrounding the vessel is sufficient to recognize the vessel based on the light transmitted, scattered, or reflected by the tissue, the fourth wavelength selected so that the magnitude of the absorption or scattering of the light of the fourth wavelength by the vessel is approximately equal to the magnitude of the absorption or scattering of the light of the fourth wavelength by the tissue surrounding the vessel.

6. The method of claim 5, further comprising correlating the light of the third wavelength transmitted, scattered, or reflected by the tissue with the light of the fourth wavelength transmitted, scattered, or reflected by the tissue to determine a position of the vessel in the tissue surrounding the vessel.

7. The method of claim 1, wherein the marker is a luminescent marker.

8. The method of claim 7, further comprising analyzing luminescent light emitted from the marker to determine a parameter of the vessel.

9. The method of claim 8, wherein the parameter of the vessel is a size of the vessel, further comprising generating an alarm signal when the size of the vessel reaches a predetermined size.

10. An energy-based tissue-sealing system, comprising:

a tissue-sealing instrument including:

a first jaw member made of a transparent or semitransparent material;

a second jaw member disposed opposite the first jaw member, the first jaw member and the second jaw member operable to move in opposite directions to grasp tissue which includes a vessel;

a transparent or semi-transparent contact coupled to the first jaw member, the transparent or semi-transparent contact configured to apply energy to the tissue to seal the tissue; and an optical system coupled to the second jaw member, the optical system configured to illuminate tissue with light having a first wavelength and a second wavelength and to form a spatial distribution of the light transmitted by the tissue into an image of the tissue, wherein the image is projected from the second jaw member; and a generator coupled to the tissue-sealing instrument, wherein the generator includes a processor configured to correlate light of the first wavelength transmitted, scattered, or reflected by the tissue with light of the second wavelength transmitted, scattered, or reflected by the tissue and configured to determine parameters of the tissue and a position of the vessel within the tissue based on the correlation between the light of the first wavelength and the light of the second wavelength, wherein the first jaw member is configured to transmit the light transmitted or scattered by the tissue to an exterior surface of the first jaw member, wherein a marker is introduced into fluid flowing in the vessel to increase contrast between the vessel and the tissue, and the marker is not introduced into the tissue, wherein the processor is further configured to select the first wavelength so that a difference between absorption or scattering of the light of the first wavelength by the marker and absorption or scattering of the light of the first wavelength by the tissue is sufficient to distinguish between the vessel and the tissue in the light transmitted, scattered, or reflected by the tissue, and wherein the processor is further configured to select the second wavelength so that a difference between absorption or scattering of the light of the second wavelength by the marker and absorption or scattering of the light of the second wavelength by the tissue is not sufficient to distinguish between the vessel and the tissue in the light transmitted, scattered, or reflected by the tissue.

11. The energy-based tissue-sealing system of claim 10, wherein the optical system includes:
   a light source configured to generate light; and
   a beam former configured to form the light into the light and to illuminate the tissue with the light.

12. The energy-based tissue-sealing system of claim 11, further comprising a second transparent or semi-transparent contact coupled to the second jaw member, the second transparent or semi-transparent contact configured to apply energy to the tissue to seal the tissue,
   wherein the optical system is disposed between the second transparent or semi-transparent contact and at least a portion of the second jaw member.

13. The energy-based tissue-sealing system of claim 10, further comprising an optical sensor coupled to the exterior surface of the first jaw member, the optical sensor configured to sense the light transmitted to the exterior surface of the first jaw member.

14. The energy-based tissue-sealing system of claim 13, wherein the optical sensor is a matrix of optical detectors.

15. The energy-based tissue-sealing system of claim 10, wherein the first jaw member is further configured to display the light transmitted or scattered by the tissue to a user of the tissue-sealing instrument.

16. The energy-based tissue-sealing system of claim 15, wherein the first jaw member includes a lens configured to display the light transmitted or scattered by the tissue to a user of the tissue-sealing instrument.

* * * * *